US012797041B2

(12) United States Patent
Li et al.

(10) Patent No.: US 12,797,041 B2
(45) Date of Patent: Nov. 17, 2026

(54) ELASTOGRAPHY METHOD, SYSTEM AND STORAGE MEDIUM

(71) Applicant: SHENZHEN MINDRAY BIO-MEDICAL ELECTRONICS CO., LTD., Shenzhen (CN)

(72) Inventors: Shuangshuang Li, Shenzhen (CN); Bangxin Lan, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 267 days.

(21) Appl. No.: 17/968,640

(22) Filed: Oct. 18, 2022

(65) Prior Publication Data

US 2023/0037641 A1 Feb. 9, 2023

Related U.S. Application Data

(63) Continuation of application No. PCT/CN2020/087701, filed on Apr. 29, 2020.

(51) Int. Cl.
*A61B 8/00* (2006.01)
*A61B 8/14* (2006.01)

(52) U.S. Cl.
CPC ............. *A61B 8/485* (2013.01); *A61B 8/463* (2013.01); *A61B 8/5223* (2013.01); *A61B 8/54* (2013.01); *A61B 8/14* (2013.01)

(58) Field of Classification Search
None
See application file for complete search history.

(56) References Cited

U.S. PATENT DOCUMENTS 8,951,198 B2 2/2015 Tamura
9,211,111 B2 12/2015 Tamura
(Continued)

FOREIGN PATENT DOCUMENTS

CN 104203115 A 12/2014
CN 104244838 A 12/2014
(Continued)

OTHER PUBLICATIONS

Second Office Action dated Aug. 12, 2024, issued in related Chinese Application No. 202080050608.9, with English machine translation (11 pages).

(Continued)

*Primary Examiner* — Shahdeep Mohammed
(74) *Attorney, Agent, or Firm* — Sheppard Mullin Richter & Hampton LLP

(57) ABSTRACT

Disclosed are an elasticity imaging method, a system and a storage medium. The method comprises: controlling an ultrasonic probe to transmit first ultrasound waves to a target object to generate shear waves propagating in a region of interest of the target object; controlling the ultrasonic probe to transmit second ultrasonic waves to the ROI to track the shear waves propagating in the ROI and receive echoes of the second ultrasonic waves, and acquiring second ultrasonic echo data based on the echoes of the second ultrasonic waves; generating a shear wave elasticity image and a strain elasticity image based on the second ultrasonic echo data; and displaying the shear wave elasticity image and the strain elasticity image. As such, the strain elasticity data is calculated according to the shear wave detection data, to enable the combination of shear wave elasticity imaging and strain elasticity imaging.

17 Claims, 8 Drawing Sheets

(56) References Cited

U.S. PATENT DOCUMENTS

| | | | | |
|---|---|---|---|---|
| 10,390,796 | B2 | 8/2019 | Fan et al. | |
| 2010/0256494 | A1* | 10/2010 | Azuma | A61B 8/485 600/443 |
| 2015/0087980 | A1* | 3/2015 | Yao | A61B 8/463 600/440 |
| 2015/0209013 | A1 | 7/2015 | Tsymbalenko | |
| 2018/0125460 | A1* | 5/2018 | Perrey | A61B 8/523 |
| 2018/0284250 | A1* | 10/2018 | Bjaerum | G01S 7/52085 |
| 2019/0012432 | A1* | 1/2019 | Sokulin | G06T 7/0012 |
| 2019/0183461 | A1 | 6/2019 | Sonoyama | |
| 2019/0254629 | A1 | 8/2019 | Li et al. | |
| 2021/0038196 | A1* | 2/2021 | Li | A61B 8/461 |

FOREIGN PATENT DOCUMENTS

| | | | |
|---|---|---|---|
| CN | 104688266 | A | 6/2015 |
| CN | 105266851 | A | 1/2016 |
| CN | 109561883 | A | 4/2019 |
| CN | 110604598 | A | 12/2019 |
| KR | 10-2015-0130093 | A | 11/2015 |
| WO | WO 2019/205166 | * | 10/2019 |

OTHER PUBLICATIONS

First Office Action and Search Report dated Feb. 22, 2024, issued in related Chinese Application No. 202080050608.9, with English machine translation (7 pages).

PCT International Preliminary Report on Patentability mailed Nov. 10, 2022, issued in related International Application No. PCT/CN2020/087701, with English translation (14 pages).

PCT International Search Report and the Written Opinion mailed Jan. 27, 2021, issued in related International Application No. PCT/CN2020/087701, with partial English translation (11 pages).

Third Office Action and Supplementary Search Report dated Nov. 18, 2024, issued in related Chinese Application No. 202080050608.9, with English machine translation (18 pages).

* cited by examiner

ELASTOGRAPHY METHOD, SYSTEM AND STORAGE MEDIUM

CROSS-REFERENCE TO RELATED APPLICATION

This is a continuation application of International Patent Application No. PCT/CN2020/087701 filed with the China National Intellectual Property Administration (CNIPA) on Apr. 29, 2020. The entire content of the above-identified application is incorporated herein by reference.

TECHNICAL FIELD

The present disclosure relates to elastography, and more particularly to elasticity imaging methods, systems and storage media.

BACKGROUND OF THE INVENTION

Ultrasound elasticity imaging has been more widely used in clinical research and diagnosis in recent years. It can qualitatively reflect the degree of hardness or softness of lesions relative to surrounding tissues or quantitatively reflect the degree of hardness or softness of lesions and surrounding tissues; accordingly, it is used clinically in thyroid, breast, musculoskeletal system, liver, vascular elasticity and so on at present. Judging the degree of hardness or softness of tissues can effectively assist in the diagnosis and evaluation of cancer lesions, benign and malignant tumors, and postoperative recovery.

Conventional elasticity imaging (compression elasticity imaging) is implemented by pressing tissue with a probe, calculating the displacement and strain of the tissue in real time to reflect parameters related to the elasticity of the tissue in a region of interest (ROI) and performing imaging, which also indirectly represents the degree of hardness or softness of various tissues. However, due to the operation of pressing on the tissue conducted by a human each time, it is difficult to keep the pressure transmitted by the probe consistent. The pressing degree and frequencies of different operators may also be different; so the repeatability and stability of strain elasticity imaging are hard to guarantee.

Shear wave elasticity imaging is implemented by exciting a focused ultrasound beam by a conventional ultrasonic probe to form an acoustic radiation force to make a shear wave source in the tissue and generate transversely propagating shear waves, recognizing and detecting the shear waves and propagation parameters thereof (such as a propagation velocity or Young's modulus that can be calculated from a propagation velocity and a density), and performing imaging on the parameters, thereby quantitatively and visually obtaining the hardness difference in the tissue. Since the excitation of the shear waves is from the acoustic radiation force generated by the focused ultrasound beam without depending on the pressure exerted by an operator, the mode of shear wave elasticity imaging is thus improved in stability and repeatability compared with strain elasticity imaging. In addition, such quantitative measurement for shear waves also make a doctor's diagnosis more objective; accordingly, it is an elasticity imaging method that doctors currently use more frequently. However, shear wave elasticity imaging is inferior to strain elasticity imaging in the delineation of lesion morphology and image resolution. At present, there is no technology on the market that combines the advantages of shear wave elasticity imaging with the advantages of strain elasticity imaging to simultaneously achieve high resolution and quantitative measurement.

SUMMARY OF THE INVENTION

The present disclosure provides an elasticity imaging solution, in which strain elasticity data can be calculated based on shear wave detection data, thereby realizing the combination of shear wave elasticity imaging and strain elasticity imaging. The elasticity imaging solution proposed by the present disclosure is briefly described below, and more details are described in the specific embodiments later in conjunction with the accompanying drawings.

In an aspect of the present disclosure, an elasticity imaging method is provided. The method may include: controlling an ultrasonic probe to transmit first ultrasonic waves to a target object to generate shear waves propagating in a region of interest of the target object; controlling the ultrasonic probe to transmit second ultrasonic waves to the region of interest to track the shear waves propagating in the region of interest and receive echoes of the second ultrasonic waves to acquire second ultrasonic echo data based on the echoes of the second ultrasonic waves; generating a shear wave elasticity image based on the second ultrasonic echo data, and generating a strain elasticity image based on the second ultrasonic echo data; and displaying the shear wave elasticity image and the strain elasticity image.

In another aspect of the present disclosure, an elasticity imaging method is provided. The method may include: controlling an ultrasonic probe to transmit first ultrasonic waves to a target object to generate shear waves propagating in a region of interest of the target object; controlling the ultrasonic probe to transmit second ultrasonic waves to the region of interest to track shear waves propagating in the region of interest and receive echoes of the second ultrasonic waves to acquire second ultrasonic echo data based on the echoes of the second ultrasonic wave; generating a shear wave elasticity image based on the second ultrasonic echo data; controlling the ultrasonic probe to at least transmit third ultrasonic waves to the region of interest and receive echoes of the third ultrasonic waves to acquire third ultrasonic echo data based on the echoes of the third ultrasonic waves; generating a strain elasticity image based on the third ultrasonic echo data; and displaying the shear wave elasticity image and the strain elasticity image.

In yet another aspect of the present disclosure, an elasticity imaging method is provided. The method may include: controlling an ultrasonic probe to transmit first ultrasonic waves to a target object to generate shear waves propagating in a region of interest of the target object; controlling the ultrasonic probe to transmit second ultrasonic waves to the region of interest to track shear waves propagating in the region of interest and receive echoes of the second ultrasonic waves to acquire second ultrasonic echo data based on the echoes of the second ultrasonic wave; generating a shear wave elasticity image based on the second ultrasonic echo data; controlling the ultrasonic probe to at least transmit third ultrasonic waves to the region of interest and receive echoes of the third ultrasonic waves to acquire third ultrasonic echo data based on the echoes of the third ultrasonic waves; generating a strain elasticity image based on the second ultrasonic echo data and the third ultrasonic echo data; and displaying the shear wave elasticity image and the strain elasticity image.

In yet another aspect of the present disclosure, an elasticity imaging system is provided. The system may include an ultrasonic probe, a transmitting/receiving sequence controller, a processor and a display device, wherein: the transmitting/receiving sequence controller is configured for controlling an ultrasonic probe to transmit first ultrasonic waves to a target object to generate shear waves propagating in a region of interest of the target object; the transmitting/receiving sequence controller is also configured for controlling the ultrasonic probe to transmit second ultrasonic waves to the region of interest to track the shear waves propagating in the region of interest and receive echoes of the second ultrasonic waves to acquire second ultrasonic echo data based on the echoes of the second ultrasonic waves; the processor is configured for generating a shear wave elasticity image based on the second ultrasonic echo data, and generating a strain elasticity image based on the second ultrasonic echo data; and the display device is configured for displaying the shear wave elasticity image and the strain elasticity image.

In yet another aspect of the present disclosure, an elasticity imaging system is provided. The system may include an ultrasonic probe, a transmitting/receiving sequence controller, a processor and a display device, wherein: the transmitting/receiving sequence controller is configured for controlling an ultrasonic probe to transmit first ultrasonic waves to a target object to generate shear waves propagating in a region of interest of the target object; the transmitting/receiving sequence controller is also configured for controlling the ultrasonic probe to transmit second ultrasonic waves to the region of interest to track shear waves propagating in the region of interest and receive echoes of the second ultrasonic waves to acquire second ultrasonic echo data based on the echoes of the second ultrasonic wave; the processor is configured for generating a shear wave elasticity image based on the second ultrasonic echo data; the transmitting/receiving sequence controller is also configured for controlling the ultrasonic probe to at least transmit third ultrasonic waves to the region of interest and receive echoes of the third ultrasonic waves to acquire third ultrasonic echo data based on the echoes of the third ultrasonic waves; the processor is also configured for generating a strain elasticity image based on the third ultrasonic echo data; and the display device is configured for displaying the shear wave elasticity image and the strain elasticity image.

In yet another aspect of the present disclosure, an elasticity imaging system is provided. The system may include an ultrasonic probe, a transmitting/receiving sequence controller, a processor and a display device, wherein: the transmitting/receiving sequence controller is configured for controlling an ultrasonic probe to transmit first ultrasonic waves to a target object to generate shear waves propagating in a region of interest of the target object; the transmitting/receiving sequence controller is also configured for controlling the ultrasonic probe to transmit second ultrasonic waves to the region of interest to track shear waves propagating in the region of interest and receive echoes of the second ultrasonic waves to acquire second ultrasonic echo data based on the echoes of the second ultrasonic wave; the processor is configured for generating a shear wave elasticity image based on the second ultrasonic echo data; the transmitting/receiving sequence controller is also configured for controlling the ultrasonic probe to at least transmit third ultrasonic waves to the region of interest and receive echoes of the third ultrasonic waves to acquire third ultrasonic echo data based on the echoes of the third ultrasonic waves; the processor is also configured for generating a strain elasticity image based on the second ultrasonic echo data and the third ultrasonic echo data; and the display device is also configured for displaying the shear wave elasticity image and the strain elasticity image.

In yet another aspect of the present disclosure, an elasticity imaging system is provided. The system may include an ultrasonic probe, a transmitting/receiving sequence controller, a processor and a display device, wherein: the transmitting/receiving sequence controller is configured for controlling an ultrasonic probe to transmit first ultrasonic waves to a target object to generate shear waves propagating in a region of interest of the target object; the transmitting/receiving sequence controller is also configured for controlling the ultrasonic probe to transmit second ultrasonic waves to the region of interest to track the shear waves propagating in the region of interest and receive echoes of the second ultrasonic waves to acquire second ultrasonic echo data based on the echoes of the second ultrasonic waves; the processor is configured for generating a shear wave elasticity image based on the second ultrasonic echo data; the transmitting/receiving sequence controller is also configured for controlling the ultrasonic probe to at least transmit third ultrasonic waves to the region of interest and receive echoes of the third ultrasonic waves to acquire third ultrasonic echo data based on the echoes of the third ultrasonic waves; the processor is also configured for generating a strain elasticity image based on the second ultrasonic echo data and/or the third ultrasonic echo data; and the display device is configured for displaying the shear wave elasticity image and the strain elasticity image.

In yet another aspect of the present disclosure, an elasticity imaging system is provided. The system may include: a memory and a processor, the memory having stored thereon a computer program executed by the processor, and the computer program executing the elasticity imaging method mentioned above when being executed by the processor.

In yet another aspect of the present disclosure, a storage medium having stored thereon a computer program executing the elasticity imaging method mentioned above when being executed is provided.

With the elasticity imaging method, system and storage medium according to the embodiments of the present disclosure, in the process of shear wave elasticity imaging, the strain elasticity data is calculated based on the shear wave detection data, so that the shear wave elasticity imaging and the strain elasticity imaging can be combined and the shear wave elasticity image and the strain elasticity image can be displayed in real time, thus both qualitative judgment and quantitative measurement of the region of interest of the target object can be realized by users.

DETAILED DESCRIPTION

In order to make the objectives, technical solutions, and advantages of the present disclosure clearer, example embodiments according to the present disclosure will be described in detail below with reference to the accompanying drawings. Apparently, the described embodiments are merely some rather than all of the embodiments of the present disclosure. It should be understood that the example embodiments described herein do not constitute any limitation to the present disclosure. All other embodiments derived by those skilled in the art without creative efforts on the basis of the embodiments of the present disclosure described in the present disclosure shall fall within the scope of protection of the present disclosure.

In the following description, a large number of specific details are given to provide a more thorough understanding of the present disclosure. However, it would be understood by those skilled in the art that the present disclosure can be implemented without one or more of these details. In other examples, to avoid confusion with the present disclosure, some technical features known in the art are not described.

It should be understood that the present disclosure can be implemented in different forms and should not be construed as being limited to the embodiments presented herein. On the contrary, these embodiments are provided to make the disclosure thorough and complete, and to fully convey the scope of the present disclosure to those skilled in the art.

The terms used herein are intended only to describe specific embodiments and do not constitute a limitation to the present disclosure. When used herein, the singular forms of "a", "an", and "said/the" are also intended to include plural forms, unless the context clearly indicates otherwise. It should also be appreciated that the terms "comprise" and/or "include", when used in the specification, determine the existence of described features, integers, steps, operations, elements, and/or units, but do not exclude the existence or addition of one or more other features, integers, steps, operations, elements, units, and/or groups thereof. As used herein, the term "and/or" includes any and all combinations of relevant listed items.

For a thorough understanding of the present disclosure, detailed steps and detailed structures will be provided in the following description to explain the technical solutions proposed by the present disclosure. The preferred embodiments of the present disclosure are described in detail as follows. However, in addition to these detailed descriptions, the present disclosure may further have other implementations.

Figure 1:
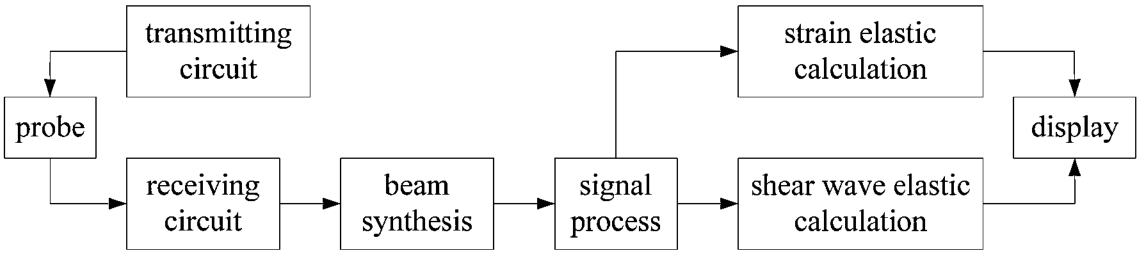
FIG. 1 is a schematic flowchart of an elasticity imaging solution in which shear wave elasticity imaging is combined with strain elasticity imaging according to an embodiment of the present disclosure.

The elasticity imaging scheme provided by the present disclosure combines shear wave elasticity imaging with strain elasticity imaging. FIG. 1 shows a schematic flowchart of an elasticity imaging solution in which shear wave imaging is combined with strain imaging according to an embodiment of the present disclosure. As shown in FIG. 1, during the calculation of shear wave elasticity, a probe may transmit special ultrasonic waves into a target tissue to generate shear waves propagating transversely; then the probe may transmit an acoustic beam to the same tissue for detecting the transmission of the shear waves and receives echoes for signal processing; and the displacement of each position of the tissue over time may be computed to calculate the propagation velocity of the shear waves, thereby generating a shear wave elasticity image and/or a shear wave elasticity parameter. For example, the shear wave elasticity parameter may be Young's modulus and the like. Strain elasticity is to calculate the displacement and strain between echo data of two frames (or two moments) at each position of the tissue by comparing the echo data of the two frames (or two moments), so as to form the strain elasticity image and/or the strain elasticity parameter; for example, the strain elasticity parameter may be a strain. When calculating the strain elasticity, if there is no displacement between the echo data of two frames (or two moments), it is impossible to calculate the strain elasticity. During the detection of the shear waves, the strain elasticity image can be obtained by calculating the strain elasticity because of a small displacement caused by natural breathing of a human body or a small displacement caused by the shaking of a probe held by a user by hand. Therefore, the elasticity imaging scheme provided in the present disclosure can be realized by combining shear wave elasticity imaging with strain elasticity imaging. In the calculation of strain elasticity, there may be a plurality of choices of echo data used, which will be described below with reference to different embodiments in conjunction with FIG. 2 to FIG. 10.

Figure 2:
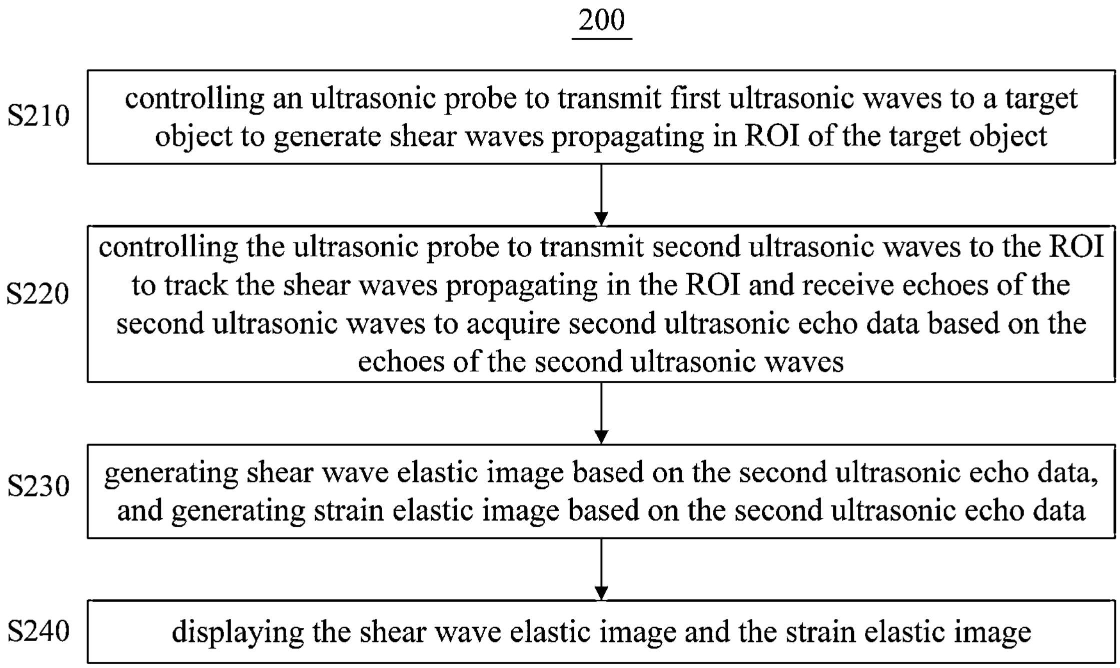
FIG. 2 is a schematic flowchart of an elasticity imaging method according to an embodiment of the present disclosure.

FIG. 2 shows a schematic flowchart of an elasticity imaging method 200 according to an embodiment of the present disclosure. As shown in FIG. 2, the elasticity imaging method 200 may include the following steps:

step S210: controlling an ultrasonic probe to transmit first ultrasonic waves to a target object to generate shear waves propagating in a region of interest (ROI) of the target object;

step S220: controlling the ultrasonic probe to transmit second ultrasonic waves to the region of interest to track the shear waves propagating in the region of interest and receive echoes of the second ultrasonic waves to acquire second ultrasonic echo data based on the echoes of the second ultrasonic waves;

step S230: generating a shear wave elasticity image based on the second ultrasonic echo data and generating a strain elasticity image based on the second ultrasonic echo data; and step S240: displaying the shear wave elasticity image and the strain elasticity image.

In an embodiment of the present disclosure, a purpose of controlling the ultrasonic probe to transmit first ultrasonic waves to the target object is to generate shear waves; and a purpose of controlling the ultrasonic probe to transmit second ultrasonic waves to the region of interest is to detect the shear waves. Accordingly, the second ultrasonic echo data, which can be used to generate the shear wave elasticity image, can be acquired according to the echoes of the second ultrasonic waves. In this embodiment of the present disclosure, the strain elasticity image can be generated based on the second ultrasonic echo data. That is, in this embodiment of the present disclosure, the echo data that is used for the calculation of strain elasticity is the echo data of the ultrasonic waves that is used for the detection of the shear waves. Based on this, with the embodiment of the present disclosure, shear wave elasticity imaging together with strain elasticity imaging can be realized simultaneously, thus the combination of the advantages of the two can be implemented. Here, it should be noted that "simultaneous" realization of shear wave elasticity imaging together with strain elasticity imaging does not necessarily mean that the shear wave elasticity image and the strain elasticity image are generated at the same time; it may also mean that both the shear wave elasticity image and the strain elasticity image can be generated in the process of the elasticity imaging method of the present disclosure, thus both providing users with diagnostic criteria.

In the embodiment of the present disclosure, generating the strain elasticity image based on the second ultrasonic echo data in step S230 may include: acquiring echo data of at least two different moments from the second ultrasonic echo data; and generating a strain elasticity image based on the echo data of at least two different moments. As mentioned above, strain elasticity is implemented by calculating the displacement and strain between echo data of two frames (or two moments) at each position of the tissue by comparing the echo data of the two frames (or two moments); accordingly, the echo data of at least two different moments can be acquired from the second ultrasonic echo data, and at least one frame of strain elasticity image can be generated based on the echo data of at least two different moments. The generation of the strain elasticity image will be schematically described below in conjunction with FIG. 3 and FIG. 4.

Figure 3:
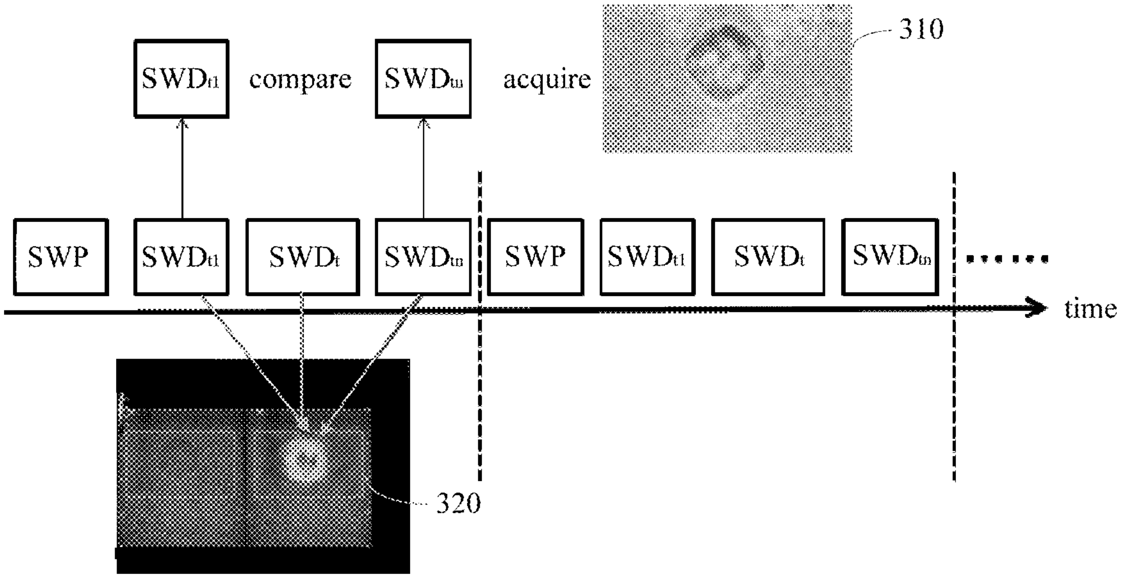
FIG. 3 is a schematic diagram showing an example of performing shear wave elasticity imaging together with strain elasticity imaging using the elasticity imaging method shown in FIG. 2.

FIG. 3 is a schematic diagram showing an example of performing shear wave elasticity imaging together with strain elasticity imaging using the elasticity imaging method shown in FIG. 2. As shown in FIG. 3, during the detection of shear waves, the probe may transmit specific focused ultrasonic shear wave pushing pulses (SWP waves for short) into the tissue to form an acoustic radiation force, which serves as a transversely propagating shear wave generated by a shear wave source. The probe then may transmit shear wave detecting pulses (SWD waves for short) to the same tissue to detect the acoustic beam transmitted by the shear waves, and receive echoes for signal processing. As shown in FIG. 3, the strain elasticity image 310 can be obtained by comparison of the echo data of SWD waves extracted at two moments before and after.

Here, in the example shown in FIG. 3, it is exemplarily shown that the echo data of SWD waves at moments t1 and tn (i.e., the echo data of $SWD_{t1}$ and the echo data of $SWD_{tn}$, where n is a natural number greater than 1) are extracted as the calculation basis of strain elasticity. The echo data of SWD waves from t1 to tn here can be used to generate a frame of shear wave elasticity image 320; that is, the echo data of two moments that is used for generating one frame of strain elasticity image may be echo data of two moments (for example, any two moments from t1 to tn in FIG. 3) for generating the same frame of shear wave elasticity image. Further, the echo data at two moments for generating one frame of strain elasticity image may be the echo data at a first moment and the echo data at a last moment (for example, t1 and tn in FIG. 3) that are used for generating the same frame of shear wave elasticity image. In other examples, the echo data at two moments for generating one frame of strain elasticity image may also be the echo data at two moments for generating shear wave elasticity images of different frames. For example, in FIG. 3, the echo data of SWD waves of one moment are extracted from the left and right sides of a dashed line respectively, where the dashed line in FIG. 3 represents a dividing line for generating each frame of shear wave elasticity image.

In addition, in the example shown in FIG. 3, a cyclic process of generating one frame of shear wave elasticity image and strain elasticity image and then regenerating one frame of shear wave elasticity image and strain elasticity image is exemplarily shown, but it should be understood that this is only an example. Such a cyclic process may not be employed in other examples. This will be described with reference to FIG. 4 below.

Figure 4:
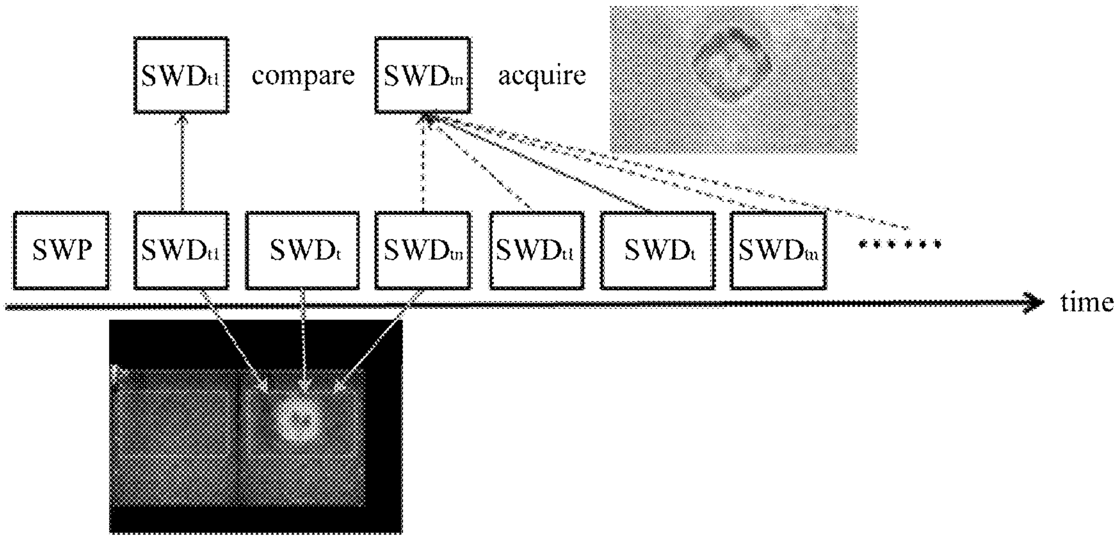
FIG. 4 is a schematic diagram showing another example of performing shear wave elasticity imaging together with strain elasticity imaging using the elasticity imaging method shown in FIG. 2.

FIG. 4 is a schematic diagram showing an example of performing shear wave elasticity imaging together with strain elasticity imaging using the elasticity imaging method shown in FIG. 2. The example shown in FIG. 4 is similar to the example shown in FIG. 3, except that in the example shown in FIG. 4, the SWP wave is transmitted once, the echo data of a first group of transmitted SWD waves (a group of waves $SWD_{t1}$ to $SWD_{tn}$ immediately after the SWP wave as shown in FIG. 4) is used to calculate a frame of shear wave elasticity image, and the echo data of the SWD waves transmitted subsequently is no longer used for the calculation of shear wave elasticity, but for the calculation of strain elasticity. Similar to the example shown in FIG. 3, in the example shown in FIG. 4, the echo data at two moments for generating one frame of strain elasticity image may be echo data at two moments for generating the same frame of shear wave elasticity image, and it may also be the echo data at two moments for generating shear wave elasticity images of different frames (although the echo data of SWD waves after the first group of SWD waves is no longer used for generating the shear wave elasticity image in the example shown in FIG. 4). For example, in FIG. 4, the echo data of SWD waves at one moment is extracted from the first group of SWD waves and the echo data of SWD waves at one moment is then extracted from the second group of SWD waves, so as to be used for strain elasticity calculation.

In a further embodiment of the present disclosure, in order to strengthen the influence of minute displacement and improve the accuracy of strain elasticity calculation, it is possible to select echo data at two moments with a long time interval (for example select echo data at the first and last moments of the same group of SWD waves in the examples shown in FIG. 3 and FIG. 4, or select echo data at two moments of different groups of SWD waves) for strain calculation. For example, a threshold is preset such that the time interval between the extracted echo data of two moments is greater than the threshold.

Figure 5A:
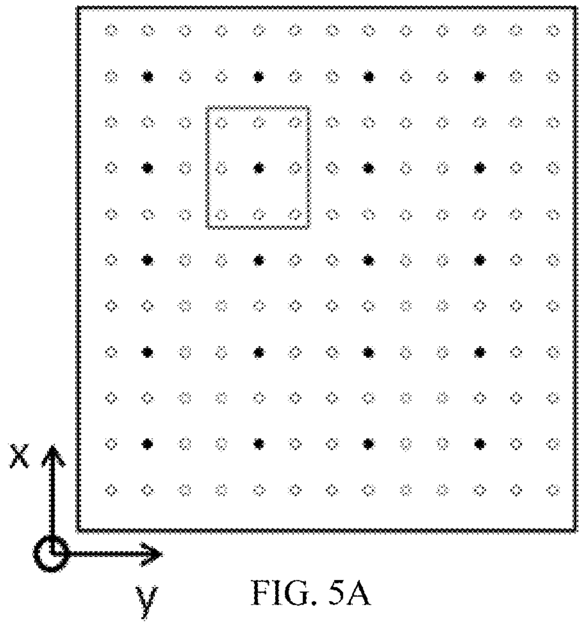
FIG. 5A, FIG. 5B and FIG. 5C are schematic diagrams showing speckle tracking in the elasticity imaging method according to an embodiment of the present disclosure.
Figure 5B:
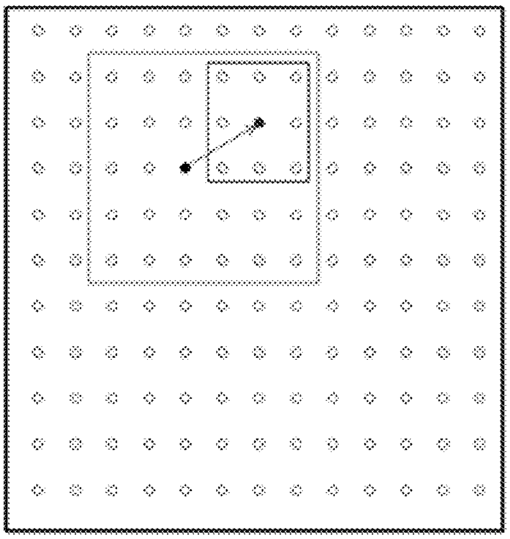
Figure 5C:
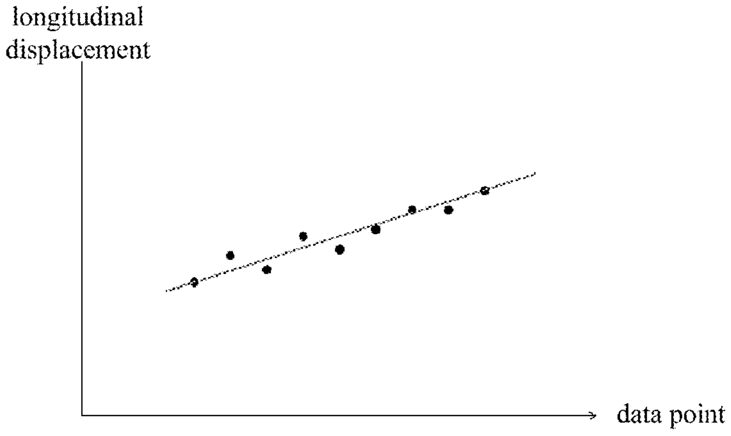

In an embodiment of the present disclosure, speckle tracking can be used to calculate the strain elasticity based on the echo data of at least two moments, which will be described in conjunction with FIGS. 5A to 5C below. FIG. 5A, FIG. 5B and FIG. 5C are schematic diagrams showing speckle tracking adopted in the elasticity imaging method according to the embodiment of the present disclosure respectively, wherein FIG. 5A is a schematic diagram of the echo data of a reference frame, FIG. 5*b* is a schematic diagram of the echo data of a current frame, and FIG. 5C is a schematic diagram of single-segment linear regression. In the schematic diagrams shown in FIG. 5A to FIG. 5C, echo data of two moments is taken as an example to describe, wherein the previous moment thereof is defined as the reference frame and the latter moment is defined as the current frame. In general, the displacement of the current frame relative to the reference frame can be obtained by speckle tracking, and the strain of the tissue can be calculated by the obtained displacement information.

Specifically, several positions may be selected in the ROI of the reference frame, and the displacement of these selected special positions in the current frame may be measured in sequence. As shown in FIG. 5A and FIG. 5B, each circle represents one data point, each black solid dot represents a selected position whose displacement needs to be calculated, and a small box encircling nine data points represents a corresponding data block. In a correlation-based displacement searching method, for a specific position such as a black solid dot in the center of the aforesaid small box, the displacement of the position (as shown by the arrow in FIG. 5B) can be acquired by searching the data block that best matches and is most correlated to the data in the small box shown in FIG. 5A (the small box included in a large box in FIG. 5B) within a search region of the data of the current frame (the aforementioned large box encircling thirty data points in FIG. 5B). The correlation can be measured by using an indicator such as the sum of the absolute value of the differences among the data blocks in two frames, the square of the differences, or a normalized correlation coefficient. After the displacements of all the special points are obtained, the special points can be divided into data of multiple lines. For each line, the positions of the special points in the y-axis direction (the transverse direction of the acoustic beam) are unchanged, but the positions in the x-axis direction (the axial direction of the acoustic beam) are different. As shown in FIG. 5A, all special points can be divided into four data lines composed of special points, and each data line has five data points. FIG. 5A is for illustration only; and there may be more than four data lines composed of special points and each line may have more than five special points in practical application. Given that there are one hundred data lines composed of special points and each data line having one hundred data points, linear regression may then be performed on the longitudinal displacements of all or part of the special points of each data line in segments, and the slope of each linear regression may represent the strain of each segment. For example, in the case of using all the special points on each line, if the length of linear regression is selected as ten special points and one point is stepped when calculating the linear regression each time, then the segments for linear regression are: 1-10 points, 2-11 points, 3-12 points, . . . , 90-99 points, 91-100 points; finally, 91 slopes (strain values) may be obtained by performing linear regression for 91 times, and 91 data points may be obtained on each strain line. For another example, in the case of using first 90 data points on each line, if the length of linear regression is selected to be 20 special points and five points are stepped when calculating the linear regression each time, then the segments for linear regression are: 1-20 points, 6-25 points, 11-30 points, . . . , 66-85 points, 71-90 points; finally, 15 slopes (strain values) may be obtained by performing linear regression for 15 times, and 15 data points may be obtained on each strain line. In this way, a strain data line corresponding to each data line can be obtained, and the data of the strain image can be obtained by combining multiple strain lines. A mode in which linear regression is performed on a single segment may be as shown in FIG. 5C.

In other embodiments of the present disclosure, the calculation of strain elasticity based on echo data of at least two moments in time may also be performed by other ways.

In a further embodiment of the present disclosure, the method 200 may also include the following steps (not shown in FIG. 2): controlling the ultrasonic probe to at least transmit third ultrasonic waves to the region of interest and receive echoes of the third ultrasonic waves to acquire third ultrasonic echo data based on the echoes of the third ultrasonic waves; generating an ultrasound image reflecting at least the ROI of tissue of the target object based on the third ultrasonic echo data; and displaying the ultrasound image. Here, the purpose of controlling the ultrasonic probe to transmit the third ultrasonic waves in the region of interest is to generate an ultrasound image of the tissue. In this embodiment, in addition to generating the shear wave elasticity image together with the strain elasticity image, the ultrasound image of the target tissue (e.g., B-mode image) may also be generated to further provide a diagnosis basis for users. Of course, in some embodiments, it may further include, after receiving the echoes of the second ultrasonic waves for the last time, control the ultrasonic probe to at least press the ROI to acquire echo data of at least two different moments from the third ultrasonic echo data, and generate a strain elasticity image based on the echo data of at least two different moments. That is, after one or several frames of shear wave elasticity images are generated, it is no longer to perform shear wave elasticity imaging and to calculate the strain elasticity image by the echo data of shear waves, instead, the strain elasticity image is obtained by B-mode echo data. The purpose of pressing the ROI is to increase the deformation of the tissue so as to improve the accuracy of the strain elasticity calculation.

In some embodiments of the present disclosure, after obtaining the shear wave elasticity image and strain elasticity image, it may, of course, also include: determining a first measuring frame in the shear wave elasticity image and a second measuring frame in the strain elasticity image; acquiring a shear wave elasticity parameter in the first measuring frame and a strain elasticity parameter in the second measuring frame; and displaying at least one of the shear wave elasticity parameter and the strain elasticity parameter. That is, after determining the measuring frames in the shear wave elasticity image and the strain elasticity image, the elasticity parameters in the corresponding measuring frames may further be calculated, wherein the shear wave elasticity parameter may be Young's modulus and the like, and the strain elasticity parameter may be strain variables and the like. Of course, the first and second measuring frames may be determined according to the features of tissues automatically recognized by the system, or be determined according to a user instruction by the system. A third measuring frame may certainly be determined in the ultrasound image, and the first measuring frame and/or the second measuring frame may be automatically matched based on the third measuring frame. The sizes of the first measuring frame, the second measuring frame and the third measuring frame may be the same or different. In addition, the first measuring frame, the second measuring frame and the third measuring frame may be displayed, and they may be displayed in different colors.

It should be noted that the shear wave elasticity image and/or the shear wave elasticity parameter, as well as the strain elasticity image and/or the strain elasticity parameter, may be displayed on a finally presented display interface in a specific display mode that is not specifically limited herein.

In an embodiment of the present disclosure, the shear wave elasticity image, the strain elasticity image and the ultrasound image generated above may be displayed independently via different display windows. Alternatively, at least two of the shear wave elasticity image, the strain elasticity image and the ultrasound image may be displayed via one display window in a superposed manner. The display scheme adopted in the elasticity imaging method according to the embodiment of the present disclosure will be described below with reference to FIG. 6A and FIG. 6B.

Figure 6A:
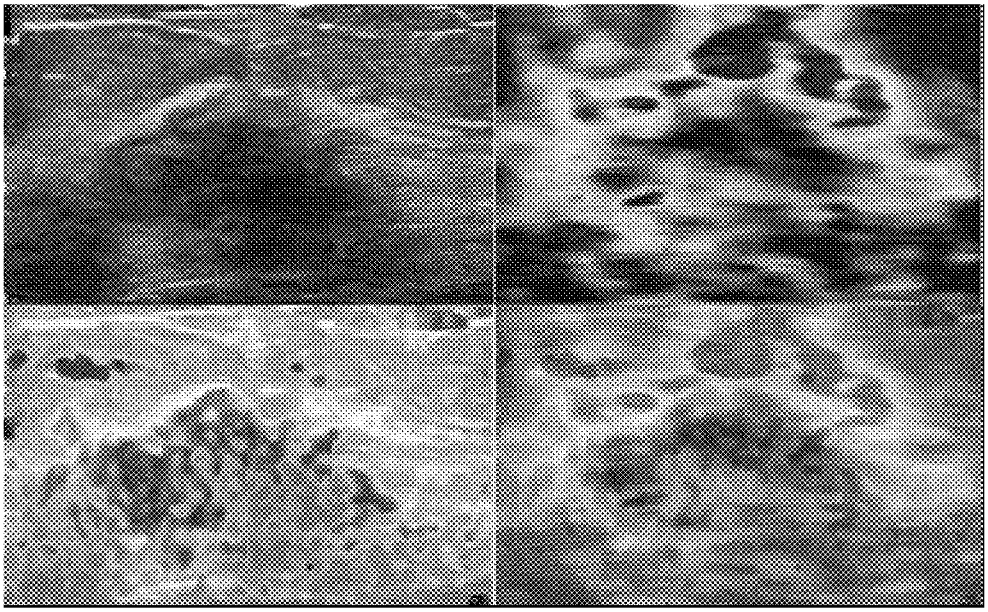
FIG. 6A and FIG. 6B are two examples of a display scheme adopted in the elasticity imaging method according to an embodiment of the present disclosure.
Figure 6B:
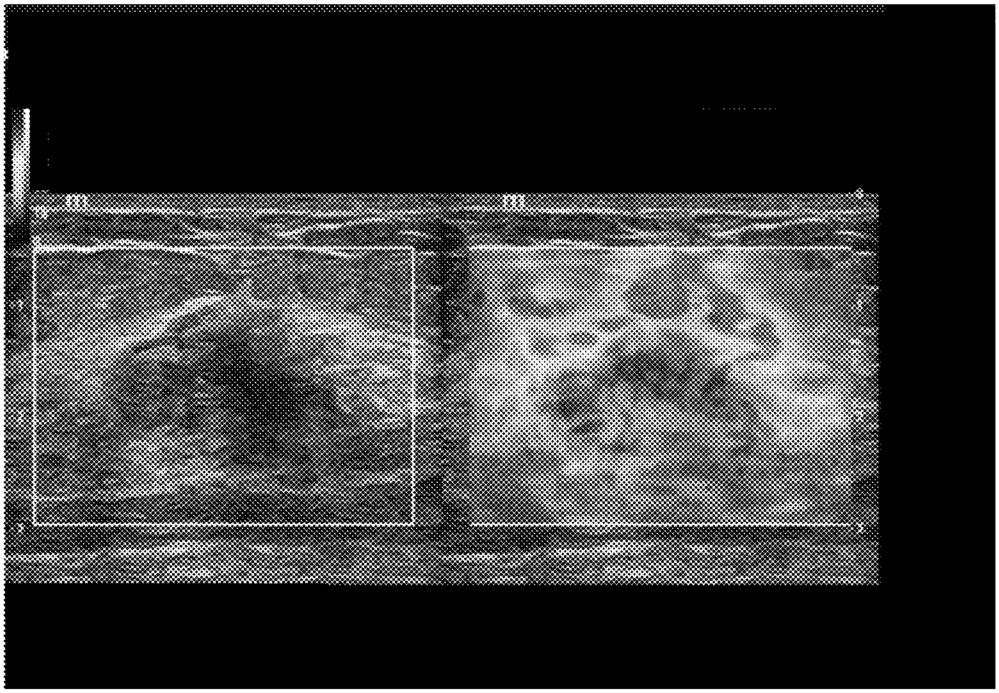

FIG. 6A and FIG. 6B show two examples of the display scheme in the elasticity imaging method according to the embodiment of the present disclosure. In the example shown in FIG. 6A, a four-window display mode is adopted, wherein the B-mode ultrasound image is displayed in a display window at the upper left corner, a superimposed image of the B-mode ultrasound image and the shear wave elasticity image is displayed in a display window at the upper right corner, a superimposed image of the B-mode ultrasound image and the strain elasticity image is displayed in a display window at the lower left corner, and a superimposed image of the first three images is displayed in a display window at the lower right corner. In the example shown in FIG. 6B, a double-window display mode is adopted, wherein the B-mode ultrasound image is displayed in the left display window, and a superimposed image of the B-mode ultrasound image, the shear wave elasticity image and the strain elasticity image is displayed in the right display window. In general, the independent display of the above images can more clearly display their respective contents, and the superposition display of two or three of the above images is helpful for users to conduct comparative analysis. In practical applications, the above images can be displayed independently or superimposed as required, or users can choose how to display the above images.

Based on the above description, with the elasticity imaging method according to the embodiment of the present disclosure, the strain elasticity data is calculated based on the shear wave detection data during shear wave elasticity imaging, so that the shear wave elasticity imaging can be combined with the strain elasticity imaging to display the shear wave elasticity image together with the strain elasticity image in real time; thereby realizing both qualitative judgment and quantitative measurement on the ROI of the target object for users.

Figure 7:
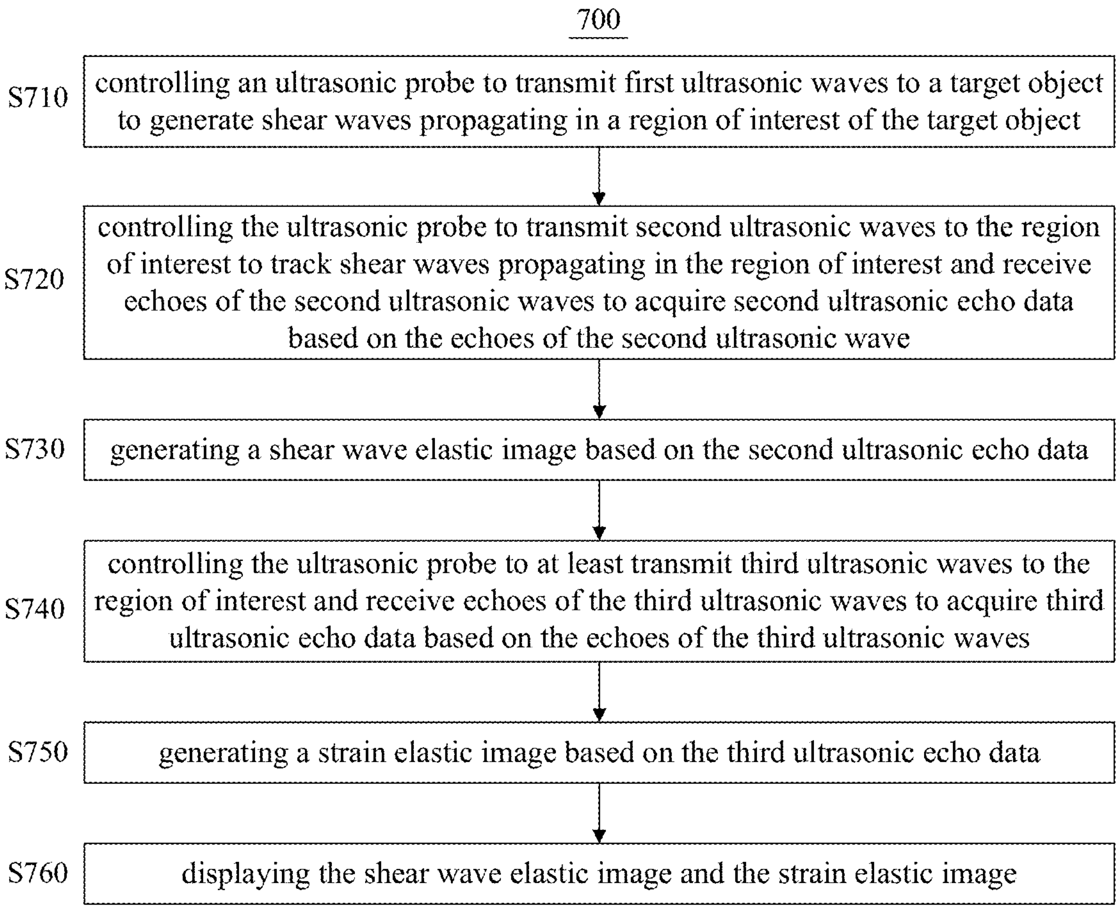
FIG. 7 is a schematic flowchart of an elasticity imaging method according to another embodiment of the present disclosure.

The elasticity imaging method according to another embodiment of the present disclosure will be described in combination with FIG. 7 to FIG. 9 below. FIG. 7 shows a schematic flowchart of an elasticity imaging method 700 according to another embodiment of the present disclosure. As shown in FIG. 7, the elasticity imaging method 700 may include the following steps:

step S710: controlling an ultrasonic probe to transmit first ultrasonic waves to a target object to generate shear waves propagating in a region of interest of the target object;

step S720: controlling the ultrasonic probe to transmit second ultrasonic waves to the region of interest to track shear waves propagating in the region of interest and receive echoes of the second ultrasonic waves to acquire second ultrasonic echo data based on the echoes of the second ultrasonic wave;

step S730: generating a shear wave elasticity image based on the second ultrasonic echo data;

step S740: controlling the ultrasonic probe to at least transmit third ultrasonic waves to the region of interest and receive echoes of the third ultrasonic waves to acquire third ultrasonic echo data based on the echoes of the third ultrasonic waves;

step S750: generating a strain elasticity image based on the third ultrasonic echo data; and step S760: displaying the shear wave elasticity image and the strain elasticity image.

In an embodiment of the present disclosure, a purpose of controlling the ultrasonic probe to transmit first ultrasonic waves to the target object is to generate shear waves; a purpose of controlling the ultrasonic probe to transmit second ultrasonic waves to the region of interest is to detect the shear waves; and a purpose of controlling the ultrasonic probe to transmit third ultrasonic waves to the region of interest is to calculate strain elasticity. Accordingly, the second ultrasonic echo data, which can be used to generate the shear wave elasticity image, can be acquired according to the echoes of the second ultrasonic waves; and the third ultrasonic echo data, which can be used to generate the ultrasound image of the tissue (e.g. B-mode ultrasound image), can be acquired according to the echoes of the third ultrasonic waves. In this embodiment of the present disclosure, the strain elasticity image can be generated according to the third ultrasonic echo data. That is, in this embodiment of the present disclosure, the echo data used for the calculation of strain elasticity is the detection data of the tissue (e.g. B-mode echo data). Based on this, with the embodiment of the present disclosure, shear wave elasticity imaging together with strain elasticity imaging can be simultaneously realized so as to achieve the combination of the advantages of the two. Here, it should be noted that “simultaneous” realization of shear wave elasticity imaging together with strain elasticity imaging does not necessarily mean that the shear wave elasticity image and the strain elasticity image are generated at the same time; it may also mean that both the shear wave elasticity image and the strain elasticity image can be generated in the process of the elasticity imaging method of the present disclosure, thus both providing users with diagnostic criteria.

In the embodiment of the present disclosure, generating the strain elasticity image based on the third ultrasonic echo data in step S750 may include: acquiring echo data of at least two different moments from the third ultrasonic echo data; and generating a strain elasticity image based on the echo data of at least two different moments. As mentioned above, strain elasticity is implemented by calculating the displacement and strain between echo data of two frames (or two moments) at each position of the tissue by comparing the echo data of the two frames (or two moments); accordingly, the echo data of at least two different moments can be acquired from the third ultrasonic echo data, and at least one frame of strain elasticity image can be generated based on the echo data of at least two different moments. The generation of the strain elasticity image will be schematically described below in conjunction with FIG. 8 and FIG. 9.

Figure 8:
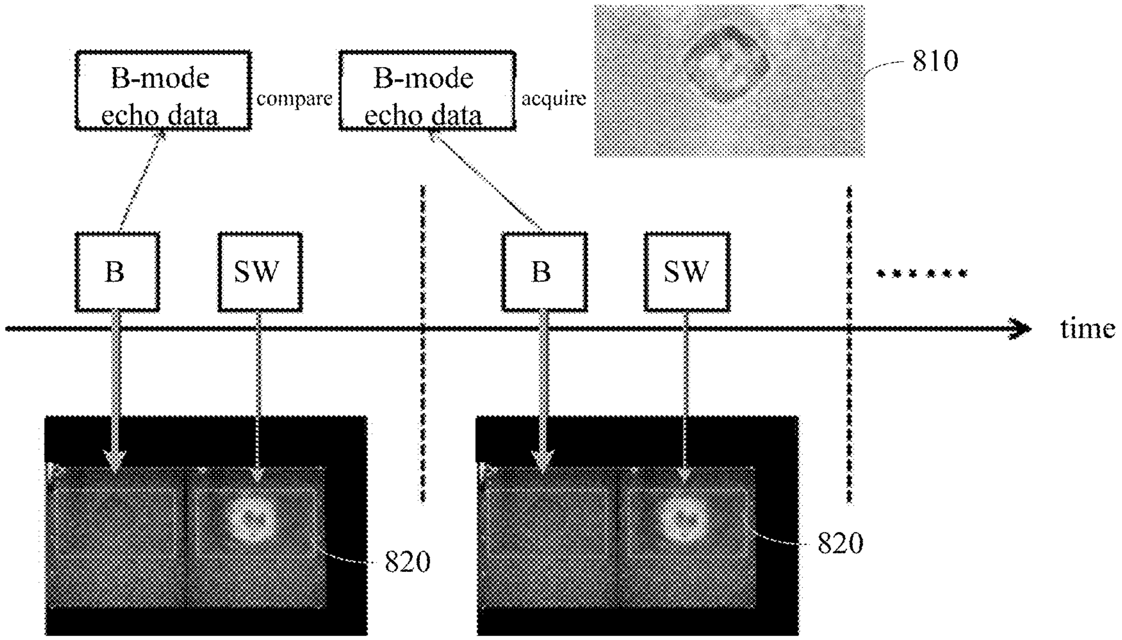
FIG. 8 is a schematic diagram showing an example of performing shear wave elasticity imaging together with strain elasticity imaging using the elasticity imaging method shown in FIG. 7.

FIG. 8 is a schematic diagram showing an example of performing shear wave elasticity imaging together with strain elasticity imaging using the elasticity imaging method shown in FIG. 7. As shown in FIG. 8, during the detection of shear waves, the tissue can also be detected at the same time; in this connection, a strain elasticity image 810 can be obtained by extracting the B-mode echo data of the two frames (or two moments) before and after and then comparing them. The shear wave elasticity image 820 can be generated from the echo data of the SW waves detecting the shear waves.

In the example shown in FIG. 8, it is exemplarily shown a cyclic process of generating one B-mode ultrasound image and one shear wave elasticity image and then regenerating one B-mode ultrasound image and one shear wave elasticity image, in which the two frames of B-mode ultrasound images can be used for generating one frame of strain elasticity image. However, it should be understood that this is only an example. Such a cyclic process may not be employed in other examples. This will be described with reference to FIG. 9 below.

Figure 9:
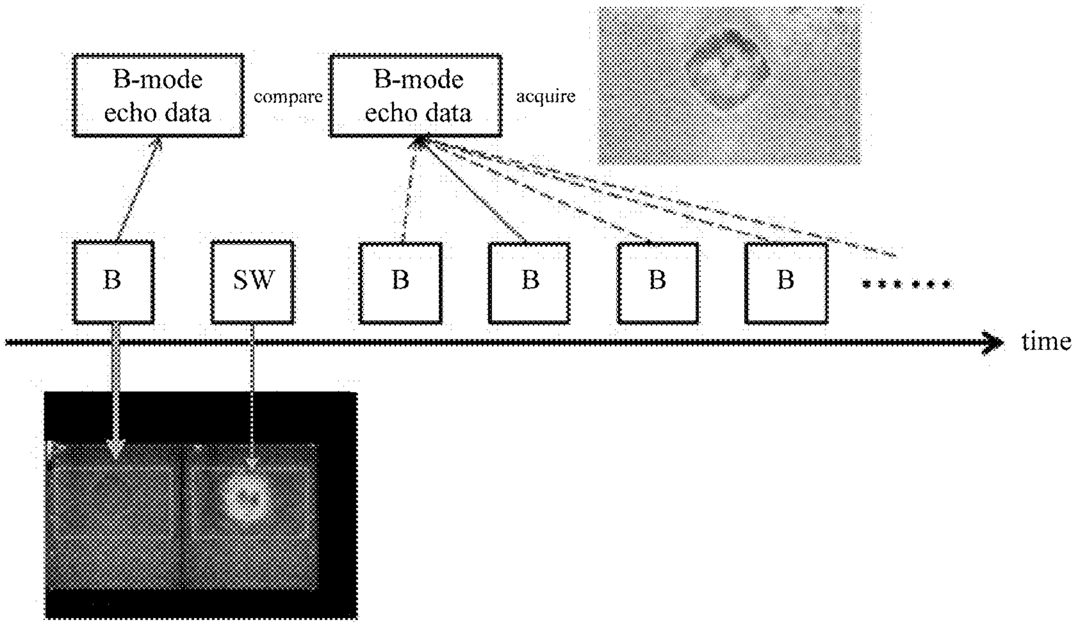
FIG. 9 is a schematic diagram showing another example of performing shear wave elasticity imaging together with strain elasticity imaging using the elasticity imaging method shown in FIG. 7.

FIG. 9 is a schematic diagram showing an example of performing shear wave elasticity imaging together with strain elasticity imaging using the elasticity imaging method shown in FIG. 7. The example shown in FIG. 9 is similar to the example shown in FIG. 8, except that in the example shown in FIG. 9, the SW wave detecting shear waves is transmitted once to calculate a frame of shear wave elasticity image, and then the shear wave elasticity image is no longer generated, but the B-mode ultrasonic waves are continuously transmitted to obtain B-mode echo data for strain elasticity calculation.

In a further embodiment of the present disclosure, in order to strengthen the influence of minute displacement and improve the accuracy of strain elasticity calculation, it is possible to select echo data at two moments with a long time interval (for example select two frames of B-mode echo data with a long time interval in the examples shown in FIG. 8 and FIG. 9). For example, a threshold is preset such that the time interval between the extracted echo data at two moments is greater than the threshold. In addition, in order to strengthen the influence of small displacement, after ending shear wave imaging, the ultrasonic probe may also be controlled to press the region of interest (the target tissue) of the target object to improve the accuracy of strain elasticity calculation. For example, after receiving the echoes of the second ultrasonic waves for the last time, the ultrasonic probe is controlled to at least press the region of interest to acquire echo data of at least two different moments from the third ultrasonic echo data, and a strain elasticity image is generated based on the echo data of at least two different moments. That is, after one or several frames of shear wave elasticity images are generated, it is no longer to perform shear wave elasticity imaging and to calculate strain elasticity image by the echo data of shear waves, instead, the strain elasticity image is obtained by B-mode echo data.

In some embodiments of the present disclosure, after obtaining the shear wave elasticity image and strain elasticity image, it may, of course, also include: determining a first measuring frame in the shear wave elasticity image and a second measuring frame in the strain elasticity image; acquiring a shear wave elasticity parameter in the first measuring frame and a strain elasticity parameter in the second measuring frame; and displaying at least one of the shear wave elasticity parameter and the strain elasticity parameter. That is, after determining the measuring frames in the shear wave elasticity image and the strain elasticity image, the elasticity parameters in the corresponding measuring frames may further be calculated, wherein the shear wave elasticity parameter may be Young's modulus and the like, and the strain elasticity parameter may be strain variables and the like. Of course, the first and second measuring frames may be determined according to the features of tissues automatically recognized by the system, or be determined according to a user instruction by the system. A third measuring frame may certainly be determined in the ultrasound image, and the first measuring frame and/or the second measuring frame may be automatically matched based on the third measuring frame. The sizes of the first measuring frame, the second measuring frame and the third measuring frame may be the same or different. In addition, the first measuring frame, the second measuring frame and the third measuring frame may be displayed, and they may be displayed in different colors.

It should be noted that the shear wave elasticity image and/or the shear wave elasticity parameter, as well as the strain elasticity image and/or the strain elasticity parameter, may be displayed on a finally presented display interface in a specific display mode that is not specifically limited herein.

In the embodiment of the present disclosure, speckle tracking may be used to calculate the strain elasticity based on the echo data of at least two moments, and the process thereof can be referred to in combination with the description in FIG. 5A to FIG. 5C above. For simplicity, it will not be repeated here. In other embodiments of the present disclosure, the strain elasticity calculation based on echo data of at least two moments in time may also be performed by other ways.

In a further embodiment of the present disclosure, the method 700 may also include the following steps (not shown in FIG. 7): based on the third ultrasonic echo data, generating an ultrasound image that reflects the tissue of at least the region of interest of the target object; and displaying the ultrasound image. In this embodiment, in addition to generating the shear wave elasticity image and the strain elasticity image, the ultrasound image (such as the B-mode image) of the target tissue may also be generated and displayed to further provide diagnosis basis for users.

In an embodiment of the present disclosure, the shear wave elasticity image, the strain elasticity image and the ultrasound image generated above may be displayed independently via different display windows, or at least two of the shear wave elasticity image, the strain elasticity image and the ultrasound image may be displayed via one display window in a superposed manner. The display scheme in the elasticity imaging method according to the embodiment of the present disclosure can be understood with reference to the above description in combination with FIG. 6A and FIG. 6B. For simplicity, it will not be repeated here. In general, the independent display of the shear wave elasticity image, the strain elasticity image and the ultrasound image generated above can more clearly display their respective contents, and the superposition display of two or three of the above images is helpful for users to conduct comparative analysis. In practical applications, the shear wave elasticity image, the strain elasticity image and the ultrasound image generated above can be displayed independently or superimposed as required, or users can choose how to display the above images. In addition, at least one of the shear wave elasticity image, strain elasticity image and ultrasound image can be displayed in real time.

Based on the above description, with the elasticity imaging method according to the embodiment of the present disclosure, during shear wave elasticity imaging, the strain elasticity data is calculated based on the detection data of the tissue, so that it is able to combine shear wave elasticity imaging with strain elasticity imaging to display the shear wave elasticity image and the strain elasticity image in real time; thereby both qualitative judgment and quantitative measurement on the region of interest of the target object can be realized for users.

Figure 10:
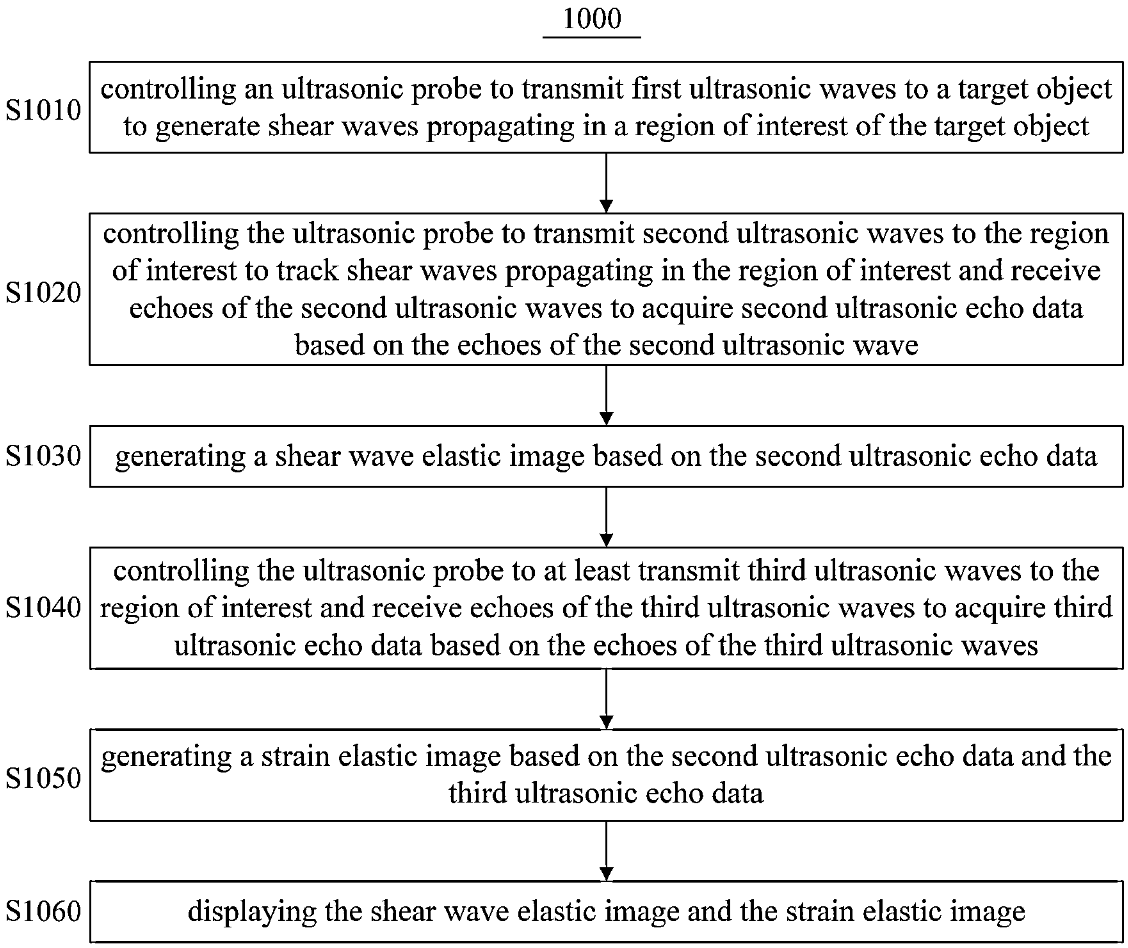
FIG. 10 is a schematic flowchart of another elasticity imaging method according to an embodiment of the present disclosure.

The elasticity imaging method according to another embodiment of the present disclosure will be described in combination with FIG. 10 below. FIG. 10 shows a schematic flowchart of an elasticity imaging method 1000 according to another embodiment of the present disclosure. As shown in FIG. 10, the elasticity imaging method 1000 may include the following steps:

step S1010: controlling an ultrasonic probe to transmit first ultrasonic waves to a target object to generate shear waves propagating in a region of interest of the target object;

step S1020: controlling the ultrasonic probe to transmit second ultrasonic waves to the region of interest to track shear waves propagating in the region of interest and receive echoes of the second ultrasonic waves to acquire second ultrasonic echo data based on the echoes of the second ultrasonic wave;

step S1030: generating a shear wave elasticity image based on the second ultrasonic echo data;

step S1040: controlling the ultrasonic probe to at least transmit third ultrasonic waves to the region of interest and receive echoes of the third ultrasonic waves to acquire third ultrasonic echo data based on the echoes of the third ultrasonic waves;

step S1050: generating a strain elasticity image based on the second ultrasonic echo data and the third ultrasonic echo data; and step S1060: displaying the shear wave elasticity image and the strain elasticity image.

In an embodiment of the present disclosure, a purpose of controlling the ultrasonic probe to transmit first ultrasonic waves to the target object is to generate shear waves; a purpose of controlling the ultrasonic probe to transmit second ultrasonic waves to the region of interest is to detect the shear waves; and a purpose of controlling the ultrasonic probe to transmit third ultrasonic waves to the region of interest is to calculate strain elasticity. Accordingly, the second ultrasonic echo data, which can be used to generate the shear wave elasticity image, can be acquired according to the echoes of the second ultrasonic waves; and the third ultrasonic echo data, which can be used to generate the ultrasound image of the tissue (e.g. B-mode ultrasound image), can be acquired according to the echoes of the third ultrasonic waves. In this embodiment of the present disclosure, the strain elasticity image can be generated according to the second ultrasonic echo data and the third ultrasonic echo data. That is, in this embodiment of the present disclosure, the echo data used for the calculation of strain elasticity is the detection data of the tissue (e.g. B-mode echo data) and the echo data of ultrasonic waves used for detecting shear waves. Based on this, with the embodiment of the present disclosure, shear wave elasticity imaging together with strain elasticity imaging can be simultaneously realized so as to achieve the combination of the advantages of the two. Here, it should be noted that "simultaneous" realization of shear wave elasticity imaging together with strain elasticity imaging does not necessarily mean that the shear wave elasticity image and the strain elasticity image are generated at the same time; it may also mean that both the shear wave elasticity image and the strain elasticity image can be generated in the process of the elasticity imaging method of the present disclosure, thus both providing users with diagnostic criteria.

In an embodiment of the present disclosure, generating a strain elasticity image based on the second ultrasonic echo data and the third ultrasonic echo data in step S1050 may comprise: acquiring echo data of at least a first moment from the second ultrasonic echo data; acquiring echo data of at least a second moment from the third ultrasonic echo data; and generating a strain elasticity image based on the echo data of at least two different moments acquired respectively from the second ultrasonic echo data and the third ultrasonic echo data. As mentioned above, strain elasticity is implemented by calculating the displacement and strain between echo data of two frames (or two moments) at each position of the tissue by comparing the echo data of the two frames (or two moments); accordingly, the echo data of at least one moment can be acquired from the second ultrasonic echo data and the third ultrasonic echo data respectively, and at least one frame of strain elasticity image can be generated based on the echo data of at least two different moments.

In a further embodiment of the present disclosure, in order to strengthen the influence of minute displacement and improve the accuracy of strain elasticity calculation, it is possible to select echo data at two moments with a long time interval (for example select B-mode echo data and the echo data of ultrasonic waves detecting the shear waves with a long time interval). For example, a threshold is preset such that the time interval between the extracted echo data at two moments is greater than the threshold. In addition, in order to strengthen the influence of small displacement, after receiving the echoes of the second ultrasonic waves for the last time, the ultrasonic probe is controlled to at least press the region of interest (target tissue) to acquire echo data of at least two different moments from the third ultrasonic echo data, and a strain elasticity image is generated based on the echo data of at least two different moments, thereby improving the accuracy of strain elasticity calculation.

In some embodiments of the present disclosure, after obtaining the shear wave elasticity image and strain elasticity image, it may, of course, also include: determining a first measuring frame in the shear wave elasticity image and a second measuring frame in the strain elasticity image; acquiring a shear wave elasticity parameter in the first measuring frame and a strain elasticity parameter in the second measuring frame; and displaying at least one of the shear wave elasticity parameter and the strain elasticity parameter. That is, after determining the measuring frames in the shear wave elasticity image and the strain elasticity image, the elasticity parameters in the corresponding measuring frames may further be calculated, wherein the shear wave elasticity parameter may be Young's modulus and the like, and the strain elasticity parameter may be strain variables and the like. Of course, the first and second measuring frames may be determined according to the features of tissues automatically recognized by the system, or be determined according to a user instruction by the system. A third measuring frame may certainly be determined in the ultrasound image, and the first measuring frame and/or the second measuring frame may be automatically matched based on the third measuring frame. The sizes of the first measuring frame, the second measuring frame and the third measuring frame may be the same or different. In addition, the first measuring frame, the second measuring frame and the third measuring frame may be displayed, and they may be displayed in different colors.

It should be noted that the shear wave elasticity image and/or the shear wave elasticity parameter, as well as the strain elasticity image and/or the strain elasticity parameter, may be displayed on a finally presented display interface in a specific display mode that is not specifically limited herein.

In an embodiment of the present disclosure, generating a strain elasticity image based on the echo data of at least two different moments acquired respectively from the second ultrasonic echo data and the third ultrasonic echo data may comprise: performing speckle tracking on the echo data of at least two different moments acquired respectively from the second ultrasonic echo data and the third ultrasonic echo data to generate the strain elasticity image. The process thereof can be referred to in combination with the description in FIG. 5A to FIG. 5C above. For simplicity, it will not be repeated here. In other embodiments of the present disclosure, the strain elasticity calculation based on echo data of at least two moments in time may also be performed by other ways.

In a further embodiment of the present disclosure, the method 1000 may also include the following steps (not shown in FIG. 10): based on the third ultrasonic echo data, generating an ultrasound image that reflects the tissue of at least the region of interest of the target object; and displaying the ultrasound image. In this embodiment, in addition to generating the shear wave elasticity image and the strain elasticity image, the ultrasound image (such as the B-mode image) of the target tissue may also be generated and displayed to further provide diagnosis basis for users.

In an embodiment of the present disclosure, the shear wave elasticity image, the strain elasticity image and the ultrasound image generated above may be displayed independently via different display windows, or at least two of the shear wave elasticity image, the strain elasticity image and the ultrasound image may be displayed via one display window in a superposed manner. The display scheme in the elasticity imaging method according to the embodiment of the present disclosure can be understood with reference to the above description in combination with FIG. 6A and FIG. 6B. For simplicity, it will not be repeated here. In general, the independent display of the shear wave elasticity image, the strain elasticity image and the ultrasound image generated above can more clearly display their respective contents, and the superposition display of two or three of the above images is helpful for users to conduct comparative analysis. In practical applications, the shear wave elasticity image, the strain elasticity image and the ultrasound image generated above can be displayed independently or superimposed as required, or users can choose how to display the above images.

Based on the above description, with the elasticity imaging method according to the embodiment of the present disclosure, during shear wave elasticity imaging, the strain elasticity data is calculated based on the detection data of the tissue and the shear wave detection data, so that it is able to combine shear wave elasticity imaging with strain elasticity imaging to display the shear wave elasticity image and the strain elasticity image in real time; thereby both qualitative judgment and quantitative measurement on the region of interest of the target object can be realized for users.

The above examples show the elasticity imaging methods according to embodiments of the present disclosure. An elasticity imaging system according to an embodiment of the present disclosure is described with reference to FIG. 11 and FIG. 12 below, which can be used to implement the elasticity imaging method according to the embodiment of the present disclosure described above.

Figure 11:
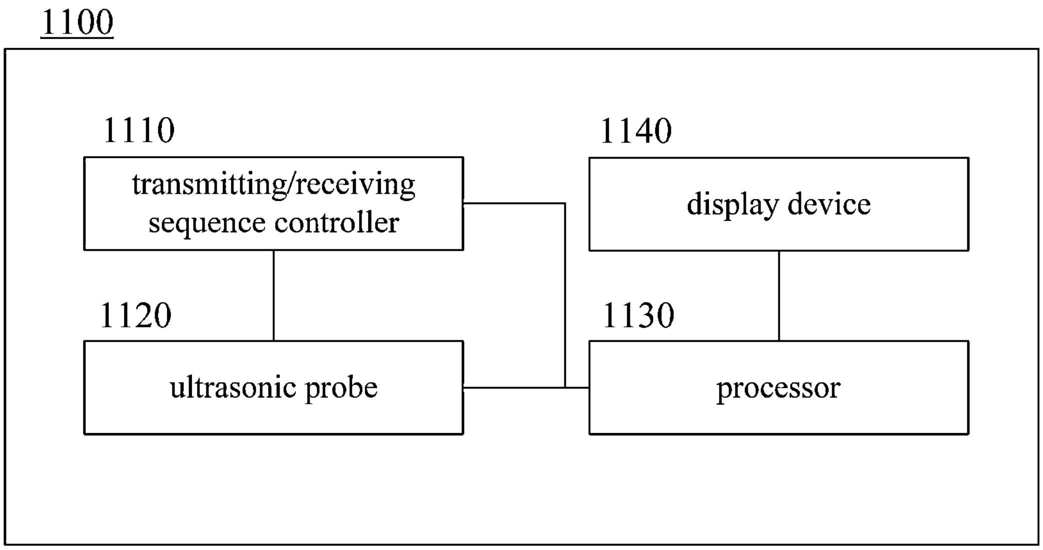
FIG. 11 is a schematic block diagram of an elasticity imaging system according to an embodiment of the present disclosure.

FIG. 11 shows a schematic block diagram of an elasticity imaging system 1100 according to an embodiment of the present disclosure. As shown in FIG. 11, the elasticity imaging system 1100 may include a transmitting/receiving sequence controller 1110, an ultrasonic probe 1120, a processor 1130 and a display device 1140. The elasticity imaging system 1100 according to the embodiment of the present disclosure can be used to realize the elasticity imaging methods 200, 700 and 1000 described above according to the embodiments of the present disclosure.

Specifically, when the elasticity imaging system 1100 is used to realize the elasticity imaging method 200 described above according to the embodiment of the present disclosure, the transmitting/receiving sequence controller 1100 is configured for controlling the ultrasonic probe 1120 to transmit first ultrasonic waves to the target object to generate shear waves propagating in a region of interest of a target object; the transmitting/receiving sequence controller 1100 is also configured for controlling the ultrasonic probe 1120 to transmit second ultrasonic waves to the region of interest to track the shear waves propagating in the region of interest and receive echoes of the second ultrasonic waves to acquire second ultrasonic echo data based on the echoes of the second ultrasonic waves; the processor 1130 is configured for generating a shear wave elasticity image based on the second ultrasonic echo data, and generating a strain elasticity image based on the second ultrasonic echo data; and the display device 1140 is configured for displaying the shear wave elasticity image and the strain elasticity image.

In an embodiment of the present disclosure, the processor 1130 generating a strain elasticity image based on the second ultrasonic echo data may comprise: acquiring echo data of at least two different moments from the second ultrasonic echo data; and generating a strain elasticity image based on the echo data of at least two different moments.

In an embodiment of the present disclosure, the echo data of at least two different moments that is configured for generating one frame of strain elasticity image is the echo data of at least two different moments that is configured for generating one same frame of shear wave elasticity image.

In an embodiment of the present disclosure, the echo data of at least two different moments that is configured for generating one frame of strain elasticity image is echo data of a first moment and echo data of a last moment that are configured for generating one same frame of shear wave elasticity image.

In an embodiment of the present disclosure, the echo data of at least two different moments that is configured for generating one frame of strain elasticity image is the echo data of two moments that is configured for generating different frames of shear wave elasticity images.

In an embodiment of the present disclosure, the processor 1130 generating a strain elasticity image based on the echo data of at least two different moments may comprise: performing speckle tracking based on the echo data of at least two different moments to generate the strain elasticity image.

In an embodiment of the present disclosure, the transmitting/receiving sequence controller 1110 may also be configured for controlling the ultrasonic probe 1120 to at least transmit third ultrasonic waves to the region of interest and receive echoes of the third ultrasonic waves to acquire third ultrasonic echo data based on the echoes of the third ultrasonic waves; the processor 1130 may also be configured for generating an ultrasound image reflecting the tissue of at least the region of interest of the target object based on the third ultrasonic echo data; and the display device 1140 may also be configured for generating the ultrasound image.

In an embodiment of the present disclosure, the shear wave elasticity image, the strain elasticity image and the ultrasound image may be displayed independently via different display windows. Alternatively, at least two of the shear wave elasticity image, the strain elasticity image and the ultrasound image may be displayed via one display window in a superimposed manner.

In an embodiment of the present disclosure, the processor 1130 may also be configured for, after receiving the echoes of the second ultrasonic waves for the last time, controlling the ultrasonic probe 1120 to at least press the region of interest to acquire echo data of at least two different moments from the third ultrasonic echo data, and generating a strain elasticity image based on the echo data of at least two different moments.

In an embodiment of the present disclosure, a time interval between the echo data of at least two different moments is greater than a preset threshold.

In an embodiment of the present disclosure, the processor 1130 may also be configured for determining a first measuring frame in the shear wave elasticity image and a second measuring frame in the strain elasticity image, and acquiring a shear wave elasticity parameter in the first measuring frame and a strain elasticity parameter in the second measuring frame; and the display device may also be configured for displaying at least one of the shear wave elasticity parameter and the strain elasticity parameter.

In an embodiment of the present disclosure, the first measuring frame and the second measuring frame are determined based on an automatic identification by the system; alternatively, the first measuring frame and the second measuring frame are determined based on an instruction operation by a user.

In an embodiment of the present disclosure, the processor may also be configured for determining a third measuring frame in the ultrasound image, and automatically determining the first measuring frame and/or the second measuring frame based on matching with the third measuring frame.

When the elasticity imaging system 1100 is used to realize the elasticity imaging method 700 described above according to the embodiment of the present disclosure, the transmitting/receiving sequence controller 1110 is configured for controlling an ultrasonic probe 1120 to transmit first ultrasonic waves to a target object to generate shear waves propagating in a region of interest of the target object; the transmitting/receiving sequence controller 1110 is also configured for controlling the ultrasonic probe 1120 to transmit second ultrasonic waves to the region of interest to track shear waves propagating in the region of interest and receive echoes of the second ultrasonic waves to acquire second ultrasonic echo data based on the echoes of the second ultrasonic wave; the processor 1130 is configured for generating a shear wave elasticity image based on the second ultrasonic echo data; the transmitting/receiving sequence controller 1110 is also configured for controlling the ultrasonic probe 1120 to at least transmit third ultrasonic waves to the region of interest and receive echoes of the third ultrasonic waves to acquire third ultrasonic echo data based on the echoes of the third ultrasonic waves; the processor 1130 is also configured for generating a strain elasticity image based on the third ultrasonic echo data; and the display device 1140 is configured for displaying the shear wave elasticity image and the strain elasticity image.

When the elasticity imaging system 1100 is used to realize the elasticity imaging method 1000 described above according to the embodiment of the present disclosure, the transmitting/receiving sequence controller 1110 is configured for controlling an ultrasonic probe 1120 to transmit first ultrasonic waves to a target object to generate shear waves propagating in a region of interest of the target object; the transmitting/receiving sequence controller 1110 is also configured for controlling the ultrasonic probe 1120 to transmit second ultrasonic waves to the region of interest to track shear waves propagating in the region of interest and receive echoes of the second ultrasonic waves to acquire second ultrasonic echo data based on the echoes of the second ultrasonic wave; the processor 1130 is configured for generating a shear wave elasticity image based on the second ultrasonic echo data; the transmitting/receiving sequence controller 1110 is also configured for controlling the ultrasonic probe 1120 to at least transmit third ultrasonic waves to the region of interest and receive echoes of the third ultrasonic waves to acquire third ultrasonic echo data based on the echoes of the third ultrasonic waves; the processor 1130 is also configured for generating a strain elasticity image based on the second ultrasonic echo data and the third ultrasonic echo data; and the display device 1140 is also configured for displaying the shear wave elasticity image and the strain elasticity image.

In an embodiment of the present disclosure, the processor 1130 generating a strain elasticity image based on the second ultrasonic echo data and the third ultrasonic echo data may comprise: acquiring echo data of at least a first moment from the second ultrasonic echo data; acquiring echo data of at least a second moment from the third ultrasonic echo data; and generating a strain elasticity image based on the echo data of at least two different moments acquired respectively from the second ultrasonic echo data and the third ultrasonic echo data.

It should be noted that when the elasticity imaging system 1100 is used to realize the elasticity imaging methods 200, 700 and 1000 of the embodiment of the present disclosure described above, and specific execution steps thereof can be referred to the description of the corresponding embodiments of the above methods 200, 700 and 1000, which will not be repeated here.

In general, the transmitting/receiving sequence controller 1110 is configured for controlling an ultrasonic probe 1120 to transmit first ultrasonic waves to a target object to generate shear waves propagating in a region of interest of the target object; the transmitting/receiving sequence controller 1110 is also configured for controlling the ultrasonic probe 1120 to transmit second ultrasonic waves to the region of interest to track the shear waves propagating in the region of interest and receive echoes of the second ultrasonic waves to acquire second ultrasonic echo data based on the echoes of the second ultrasonic waves; the processor 1130 is configured for generating a shear wave elasticity image based on the second ultrasonic echo data; and the transmitting/receiving sequence controller is also configured for controlling the ultrasonic probe to transmit at least third ultrasonic waves to the region of interest and receive echoes of the third ultrasonic waves to acquire third ultrasonic echo data based on the echoes of the third ultrasonic waves; the processor 1130 is also configured for generating a strain elasticity image based on the second ultrasonic echo data and/or the third ultrasonic echo data; and the display device 1140 is configured for displaying the shear wave elasticity image and the strain elasticity image.

Figure 12:
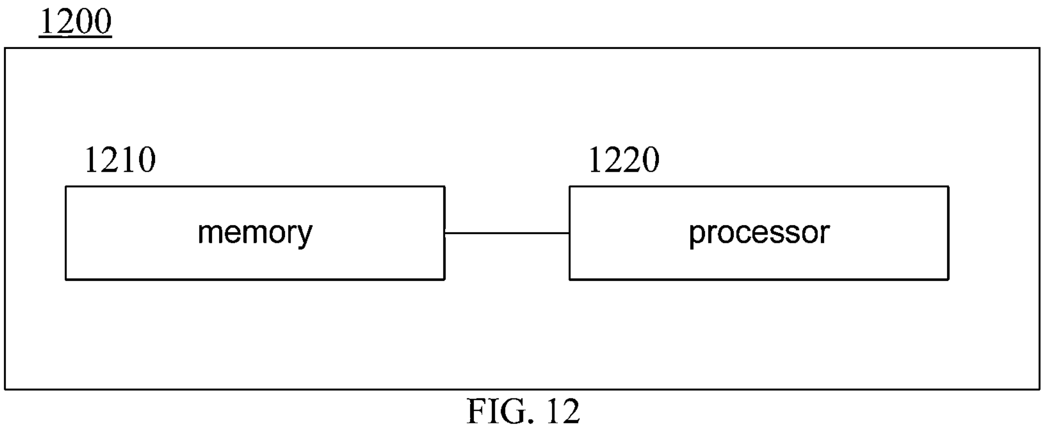
FIG. 12 is a schematic block diagram of another elasticity imaging system according to an embodiment of the present disclosure.

A schematic block diagram of the elasticity imaging system of another embodiment of the present disclosure is described with reference to FIG. 12 below. FIG. 12 shows a schematic block diagram of an elasticity imaging system 1200 according to an embodiment of the present disclosure. The elasticity imaging system 1200 includes a memory 1210 and a processor 1220.

The memory 1210 stores a program for implementing the corresponding steps in the elasticity imaging methods 200, 700 and 1000 according to the embodiment of the present disclosure. The processor 1220 is used to run the program stored in the memory 1210 to execute the corresponding steps of the elasticity imaging methods 200, 700 and 1000 according to the embodiment of the present disclosure.

In addition, according to the embodiment of the present disclosure, a storage medium is also provided, on which program instructions are stored, and when the program instructions are run by a computer or a processor, corresponding steps of the elasticity imaging methods 200, 700 and 1000 of the embodiment of the present disclosure are executed. The storage medium may include, for example, a memory card of a smart phone, a storage component of a tablet computer, a hard disk of a personal computer, a read-only memory (ROM), an erasable programmable read-only memory (EPROM), a portable compact disk read-only memory (CD-ROM), a USB memory, or any combination of the above storage media. The computer-readable storage medium may be any combination of one or more computer-readable storage media.

In addition, according to the embodiment of the present disclosure, there is also provided a computer program, which can be stored on the cloud or local storage medium. When the computer program is run by a computer or processor, it is used to execute the corresponding steps of the elasticity imaging method of the embodiment of the present disclosure.

Based on the above description, with the elasticity imaging method, the system and the storage medium according to the embodiments of the present disclosure, in the process of shear wave elasticity imaging, the strain elasticity data is calculated based on the shear wave detection data, so that the shear wave elasticity imaging and the strain elasticity imaging can be combined, and the shear wave elasticity image and the strain elasticity image can be displayed in real time, thus both qualitative judgment and quantitative measurement of the region of interest of the target object can be realized by users.

While exemplary embodiments have been described herein with reference to the accompanying drawings, it should be understood that the above example embodiments are merely illustrative and are not intended to limit the scope of the disclosure thereto. Those skilled in the art may make various changes and modifications therein without departing from the scope and spirit of the disclosure. All such changes and modifications are intended to be included in the scope of the disclosure as claimed in the appended claims.

A person of ordinary skill in the art may be aware that, in combination with the examples described in the embodiments disclosed in this specification, units and algorithm steps may be implemented by using electronic hardware or a combination of computer software and electronic hardware. Whether the functions are performed by hardware or software depends on particular applications and design constraint conditions of the technical solutions. Those skilled in the art could use different methods to implement the described functions for each particular application, but such implementation should not be considered to be beyond the scope of the disclosure.

In several embodiments provided in the present disclosure, it should be understood that the disclosed devices and methods may be implemented in other ways. For example, the device embodiments described above are merely exemplary. For example, the division of units is merely a logical function division. In actual implementations, there may be other division methods. For example, a plurality of units or components may be combined or integrated into another device, or some features may be omitted or not implemented.

A large number of specific details are explained in this specification provided herein. However, it can be understood that the embodiments of the disclosure can be practiced without these specific details. In some instances, well-known methods, structures, and technologies are not shown in detail, so as not to obscure the understanding of this description.

Similarly, it should be understood that in order to simplify the disclosure and help to understand one or more of various aspects of the disclosure, in the description of the exemplary embodiments of the disclosure, various features of the disclosure are sometimes together grouped into an individual embodiment, figure or description thereof. However, the method of the disclosure should not be construed as reflecting the following intention, namely, the disclosure set forth requires more features than those explicitly stated in each claim. More precisely, as reflected by the corresponding claims, the inventive point thereof lies in that features that are fewer than all the features of an individual embodiment disclosed may be used to solve the corresponding technical problem. Therefore, the claims in accordance with the particular embodiments are thereby explicitly incorporated into the particular embodiments, wherein each claim itself serves as an individual embodiment of the disclosure.

Those skilled in the art should understand that, in addition to the case where features are mutually exclusive, any combination may be used to combine all the features disclosed in this specification (along with the appended claims, abstract, and drawings) and all the processes or units of any of methods or devices as disclosed. Unless explicitly stated otherwise, each feature disclosed in this specification (along with the appended claims, abstract, and drawings) may be replaced by an alternative feature that provides the same, equivalent, or similar object.

Furthermore, those skilled in the art should understand that although some of the embodiments described herein comprise some but not other features included in other embodiments, combinations of features of different embodiments are meant to be within the scope of the disclosure, and form different embodiments. For example, in the claims, any one of the embodiments set forth thereby can be used in any combination.

Various embodiments regarding components in the disclosure may be implemented in hardware, or implemented by software modules running on one or more processors, or implemented in a combination thereof. It should be understood for those skilled in the art that a microprocessor or a digital signal processor (DSP) may be used in practice to implement some or all of the functions of some modules according to the embodiments of the disclosure. The disclosure may further be implemented as an apparatus program (e.g. a computer program and a computer program product) for executing some or all of the methods described herein. Such a program for implementing the disclosure may be stored on a computer-readable medium, or may be in the form of one or more signals. Such a signal may be downloaded from an Internet website, or provided on a carrier signal, or provided in any other form.

It should be noted that the description of the disclosure made in the above-mentioned embodiments is not to limit the disclosure, and those skilled in the art may design alternative embodiments without departing from the scope of the appended claims. In the claims, any reference signs placed between parentheses should not be construed as limitation on the claims. The word "comprising" does not exclude the presence of elements or steps not listed in a claim. The word "a" or "an" preceding an element does not exclude the presence of a plurality of such elements. The disclosure may be implemented by means of hardware comprising several different elements and by means of an appropriately programmed computer. In unit claims listing several ultrasound devices, several of these ultrasound devices may be specifically embodied by one and the same item of hardware. The use of the terms "first", "second", "third", etc. does not indicate any order. These terms may be interpreted as names.

The above is only the specific embodiment of the present disclosure or the description of the specific embodiment, and the protection scope of the present disclosure is not limited thereto. Any changes or substitutions should be included within the protection scope of the present disclosure. The protection scope of the present disclosure shall be subject to the protection scope of the claims.

What is claimed is:

1. An elasticity imaging method, comprising:

controlling an ultrasonic probe to transmit first ultrasonic waves to a target object to generate shear waves propagating in a region of interest of the target object;

controlling the ultrasonic probe to transmit shear wave detecting (SWD) waves to the region of interest to track the shear waves propagating in the region of interest and receive echoes of the SWD waves, and acquiring echo data of the SWD waves based on the echoes of the SWD waves;

based on a same echo data of the SWD waves, generating a shear wave elasticity image and generating a strain elasticity image, wherein the same echo data of the SWD waves is ultrasonic echo data corresponding to the SWD waves for tracking the shear waves; and displaying the shear wave elasticity image and the strain elasticity image, wherein generating the strain elasticity image based on the same echo data of the SWD waves comprises:

acquiring echo data of the SWD waves of at least two different moments from the same echo data of the SWD waves; and generating the strain elasticity image based on the echo data of the SWD waves of at least two different moments, wherein the echo data of the SWD waves of at least two different moments is used for generating one frame of the strain elasticity image.

2. The method according to claim 1, wherein the echo data of the SWD waves of at least two different moments that is configured for generating the one frame of the strain elasticity image is echo data of the SWD waves of two moments that is configured for generating different frames of shear wave elasticity images.

3. The method according to claim 1, wherein the echo data of the SWD waves of at least two different moments that is configured for generating the one frame of the strain elasticity image is the echo data of the SWD waves of at least two different moments that is configured for generating one same frame of the shear wave elasticity image.

4. The method according to claim 3, wherein the echo data of the SWD waves of at least two different moments that is configured for generating the one frame of the strain elasticity image is echo data of the SWD waves of a first moment and echo data of the SWD waves of a last moment that are configured for generating one same frame of the shear wave elasticity image.

5. The method according to claim 1, further comprising:

controlling the ultrasonic probe to at least transmit third ultrasonic waves to the region of interest and receive echoes of the third ultrasonic waves, and acquiring third ultrasonic echo data based on the echoes of the third ultrasonic waves;

generating an ultrasound image reflecting at least a tissue of the region of interest of the target object based on the third ultrasonic echo data; and displaying the ultrasound image.

6. The method according to claim 5, further comprising:

acquiring echo data of at least two different moments from the third ultrasonic echo data; and generating another strain elasticity image based on the echo data of the third ultrasonic echo data of at least two different moments.

7. The method according to claim 6, further comprising:

after receiving the echoes of the SWD waves for a last time, controlling the ultrasonic probe to at least press the region of interest to acquire the echo data of at least two different moments from the third ultrasonic echo data.

8. The method according to claim 5, further comprising:

determining a first measuring frame in the shear wave elasticity image and a second measuring frame in the strain elasticity image;

acquiring a shear wave elasticity parameter in the first measuring frame and a strain elasticity parameter in the second measuring frame; and displaying at least one of the shear wave elasticity parameter and the strain elasticity parameter.

9. The method according to claim 8, further comprising:

determining a third measuring frame in the ultrasound image, and automatically acquiring the first measuring frame and/or the second measuring frame based on matching with the third measuring frame.

10. An elasticity imaging method, comprising:

controlling an ultrasonic probe to transmit first ultrasonic waves to a target object to generate shear waves propagating in a region of interest of the target object;

controlling the ultrasonic probe to transmit shear wave detecting (SWD) waves to the region of interest to track shear waves propagating in the region of interest and receive echoes of the SWD waves, and acquiring echo data of the SWD waves based on the echoes of the SWD wave;

generating a shear wave elasticity image based on the echo data of the SWD waves;

controlling the ultrasonic probe to at least transmit third ultrasonic waves to the region of interest and receive echoes of the third ultrasonic waves, and acquiring third ultrasonic echo data based on the echoes of the third ultrasonic waves, wherein the third ultrasonic echo data is B-mode echo data for generating a B-mode ultrasound image of the target object, and the echo data of the SWD waves and the B-mode echo data are acquired alternatively, and generating a strain elasticity image based on the B-mode echo data, comprising:

acquiring echo data of at least two different moments, which comprises a moment before the echo data of the SWD waves for generating the shear wave elasticity image and a moment after the echo data of the SWD waves, from the B-mode echo data; and performing speckle tracking based on the echo data of at least two different moments to generate the strain elasticity image, wherein the echo data of the at least two different moments is used for generating one frame of the strain elasticity image; and displaying the shear wave elasticity image and the strain elasticity image.

11. The method according to claim 10, further comprising:

generating the B-mode ultrasound image reflecting at least a tissue of the region of interest of the target object based on the B-mode echo data; and displaying the B-mode ultrasound image.

12. The method according to claim 10, further comprising:

after receiving the echoes of the SWD waves for a last time, controlling the ultrasonic probe to at least press the region of interest to acquire echo data of at least two different moments from the third ultrasonic echo data, and generating the strain elasticity image based on said echo data of at least two different moments.

13. The method according to claim 10, further comprising:

determining a first measuring frame in the shear wave elasticity image and a second measuring frame in the strain elasticity image;

acquiring a shear wave elasticity parameter in the first measuring frame and a strain elasticity parameter in the second measuring frame; and displaying at least one of the shear wave elasticity parameter and the strain elasticity parameter.

14. The method according to claim 13, further comprising:

determining a third measuring frame in the B-mode ultrasound image, and automatically acquiring the first measuring frame and/or the second measuring frame based on matching with the third measuring frame.

15. An elasticity imaging method, comprising:

controlling an ultrasonic probe to transmit first ultrasonic waves to a target object to generate shear waves propagating in a region of interest of the target object;

controlling the ultrasonic probe to transmit shear wave detecting (SWD) waves to the region of interest to track shear waves propagating in the region of interest and receive echoes of the s SWD waves to acquire echo data of the SWD waves based on the echoes of the SWD waves;

controlling the ultrasonic probe to at least transmit third ultrasonic waves to the region of interest and receive echoes of the third ultrasonic waves, and acquiring third ultrasonic echo data based on the echoes of the third ultrasonic waves;

generating a shear wave elasticity image based on the echo data of the SWD waves, and generating a strain elasticity image based on a same echo data of the SWD waves and the third ultrasonic echo data, wherein the same echo data of the SWD waves is ultrasonic echo data corresponding to the SWD waves for tracking the shear waves; and displaying the shear wave elasticity image and the strain elasticity image, wherein generating the strain elasticity image based on the same echo data of the SWD waves and the third ultrasonic echo data comprises:

acquiring at least echo data of the SWD waves of a first moment from the echo data of the SWD waves;

acquiring at least echo data of a second moment from the third ultrasonic echo data; and generating the strain elasticity image at least based on the echo data of the SWD waves of the first moment and the third ultrasonic echo data of the second moment, wherein the echo data of the SWD waves of the first moment and the third ultrasonic echo data of the second moment are used for generating one frame of the strain elasticity image.

16. The method according to claim 15, further comprising:

determining a first measuring frame in the shear wave elasticity image and a second measuring frame in the strain elasticity image;

acquiring a shear wave elasticity parameter in the first measuring frame and a strain elasticity parameter in the second measuring frame; and displaying at least one of the shear wave elasticity parameter and the strain elasticity parameter.

17. The method according to claim 16, further comprising:

determining a third measuring frame in an ultrasound image, and automatically determining the first measuring frame and/or the second measuring frame based on matching with the third measuring frame.

* * * * *